United States Patent [19]

Medoff

[11] Patent Number: 4,628,923
[45] Date of Patent: Dec. 16, 1986

[54] AXIAL COMPRESSION DEVICE

[76] Inventor: Robert J. Medoff, 1896 Poplar Wood Cir. #1, Germantown, Tenn. 38138

[21] Appl. No.: 555,548

[22] Filed: Nov. 28, 1983

[51] Int. Cl.$^4$ ............................................. A61F 5/04
[52] U.S. Cl. ........................... 128/92 YV; 128/92 YK
[58] Field of Search ............. 128/92 BA, 92 BB, 92 B, 128/92 BC, 92 R

[56] References Cited

U.S. PATENT DOCUMENTS

| 2,526,959 | 10/1950 | Lorenzo | 128/92 BB |
|---|---|---|---|
| 2,612,159 | 9/1952 | Collison | 128/92 BA |
| 2,702,543 | 2/1955 | Pugh et al. | 128/92 BA |
| 2,801,631 | 8/1957 | Charnley | 128/92 BB |
| 3,374,786 | 3/1968 | Callender, Jr. | 128/92 BB |
| 3,400,711 | 9/1968 | Hux et al. | 128/92 D |
| 3,782,374 | 1/1974 | Fischer | 128/92 BB |
| 3,900,025 | 8/1975 | Barnes, Jr. | 128/92 D |
| 3,987,499 | 10/1976 | Scharbach et al. | 128/92 B |
| 3,996,931 | 12/1976 | Callender, Jr. | 128/92 BB |
| 4,095,591 | 6/1978 | Graham, Jr. et al. | 128/92 BB |
| 4,379,451 | 4/1983 | Getscher | 128/92 BE |
| 4,438,762 | 3/1984 | Kyle | 128/92 BB |
| 4,441,492 | 4/1984 | Rydell et al. | 128/92 EB |

OTHER PUBLICATIONS

Zimmer, Warsaw In., 1981 Catalog, p. B 170, "Massie Sliding Nail".

Primary Examiner—Gene Mancene
Assistant Examiner—C. W. Shedd
Attorney, Agent, or Firm—Shapiro and Shapiro

[57] ABSTRACT

An axial compression device for the fixation of a fractured bone comprises an assembly including a lag screw and a retaining member secured to bone fragments on opposite sides of a fracture and an angled slide member adapted to be connected to the lag screw and cooperable with the retaining member for providing a compressive force between the bone fragments. The lag screw and angled slide member are especially adapted to achieve simultaneous fixation of a secondary fracture which may also be present.

20 Claims, 2 Drawing Figures

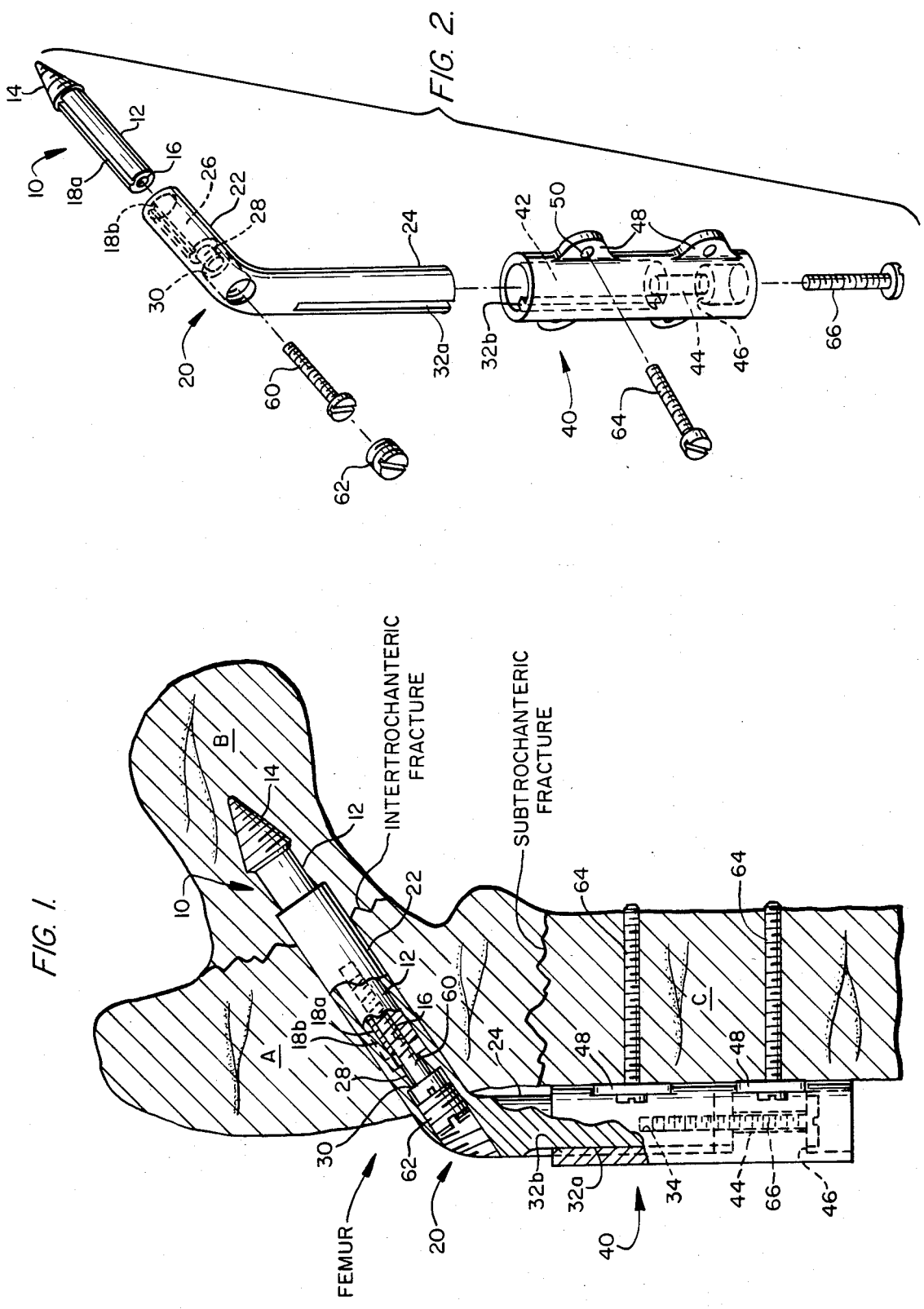

AXIAL COMPRESSION DEVICE

BACKGROUND OF THE INVENTION

This invention relates to devices for the fixation of fractured bones and in particular to a device for the fixation of fractures involving long bones, such as subtrochanteric and intertrochanteric fractures of the femur.

The successful fixation of any fractured long bone is generally dependent upon two basic considerations. First, the fracture site should be rigidly maintained in compression to stimulate bone repair; and second, shear, rotational and angular stresses at the fracture site should be minimized (and if possible eliminated) as such stresses inhibit bone union. In fractures involving the proximal aspect of the femur, for example, these considerations are particularly important due to the considerable magnitude and complex distribution of the forces to which this region is subjected. (Loads up to four times body weight may be transmitted through this region during the gait cycle.)

Heretofore, the fixation of fractures of the proximal femur has typically been attempted by the insertion of a hip compression screw, usually comprising a lag screw to be secured in the femoral head, a compression plate cooperable with the lag screw to be secured to the femoral shaft and a compression screw for attaching the compression plate to the lag screw and applying a compressive force therebetween. Such devices have also been more generally used for the fixation of fractures in which one major fragment is mostly cancellous and the other fragment is primarily cortical (e.g., supracondylar fractures of the distal femur).

Although prior hip compression devices are effective for the fixation of certain types of fracture configurations involving the proximal femur (more specifically, certain intertrochanteric fracture configurations), there are many fracture configurations for which these devices perform poorly or are ineffective. For example, in the case of subtrochanteric fractures of the proximal femur (as well fractures in other regions such as supracondular fractures of the distal femur), prior hip compression devices can allow significant shear, rotational and angular forces to occur while failing to provide the desired compressive forces at the fracture site. In practice, such characteristics may lead to a loss of reduction, nonunion or malunion of the fractured bone and even breakage of the device subsequent to insertion.

The present invention overcomes these deficiencies and other disadvantages of the prior art.

SUMMARY OF THE INVENTION

In accordance with the present invention, an axial compression device is provided whereby longitudinally adjacent segments of a fractured long bone may be placed and maintained in rigid axial compression and whereby shear, rotational and angular forces at the fracture site are minimized. More particularly, according to one of its broader aspects, the invention provides an axial compression device for the fixation of a fractured bone (such as a femur wherein both subtrochanteric and intertrochanteric fractures are present) having a first bone fragment, a second bone fragment disposed transverse to the first bone fragment and a third bone fragment disposed longitudinally of the first bone fragment, which comprises first means adapted to be secured to the second bone fragment, second means cooperable with the first means for applying a compressive force between the first and second bone fragments, and third means adapted to be secured to the third bone fragment and cooperable with the second means for applying a compressive force between the first and third bone fragments. As will be described hereinafter in connection with a preferred form of the invention, the first means may comprise a lag screw, the second means may comprise an angled slide member having a first leg adapted to be connected to the lag screw and a second leg, and the third means may comprise a retaining member adapted to be slidably coupled to the second leg of the angled slide member.

In another of its broad aspects, the invention provides an axial compression device for the fixation of a fractured bone (such as a femur wherein a subtrochanteric fracture is present) having a first bone fragment and a second bone fragment disposed longitudinally thereof, which comprises shaft means adapted to be secured within the first bone fragment, retaining means adapted to be secured to the second bone fragment, and an angled slide member having a first leg and a second leg, the first leg being adapted to be connected to the shaft means, the second leg being cooperable with the retaining means for applying a compressive force between the first and second bone fragments.

According to yet another broad aspect of the invention, an assembly is provided for use in an axial compression device for the fixation of a fractured bone of the last mentioned type, which comprises retaining means adapted to be secured to the second bone fragment and an angled slide member having a first leg and a second leg, the first leg being adapted to be connected to the first bone fragment, the second leg being cooperable with said retaining means for applying a compressive force between the first and second bone fragments.

The features and advantages of the invention will be further understood from the following description of the preferred embodiment taken in connection with the accompanying drawing.

BRIEF DESCRIPTION OF THE DRAWING

FIG. 1 is an elevation view shown partly in section of an axial compression device according to the invention applied to the proximal aspect of a right femur, and FIG. 2 is an exploded perspective view of the axial compression device of FIG. 1.

DESCRIPTION OF THE PREFERRED EMBODIMENT

FIGS. 1 and 2 illustrate a preferred axial compression device in accordance with the present invention. For the purposes of example only, the device is shown particularly adapted for the fixation of a fractured femur wherein both a subtrochanteric fracture and an intertrochanteric fracture are present. FIG. 1 depicts a right femur in such condition. More specifically, the femur in FIG. 1 includes three bone fragments: a fragment denoted by the reference letter A, a fragment transverse to fragment A and denoted by the reference letter B, and another fragment disposed longitudinally of fragment A and denoted by reference letter C. As indicated in the drawing, the intertrochanteric fracture appears between bone fragment A (which includes the greater and lesser trochanters) and bone fragment B (which includes the femoral head). The subtrochanteric fracture appears between bone fragment A and bone fragment C (which includes the upper portion of the femoral shaft). It is to be understood, of course, that while the invention will hereinafter be explained in connection with the multiply fractured femur just described, an axial compression device according to the invention may (as will be apparent from the ensuing discussion) be employed for the fixation of a variety of fracture configurations such as a subtrochanteric fracture alone or a supracondylar fracture of the distal femur.

Referring now to FIG. 2, it will be seen that the illustrated embodiment of the invention comprises shaft means such as a lag screw 10, slide means such as an angled slide member 20 and retaining means such as a barrelled side plate (retaining member) 40. These components are preferably made from a substantially rigid material of low biologic reactivity such as stainless steel, carbon fiber or one of the various cobalt alloys used for surgical purposes (as are the remaining components of the device to be discussed later). The lag screw 10 includes a cylindrical shaft portion 12 and is adapted to be secured to a bone fragment, in this case fragment B, in the standard manner by means of a threaded head portion 14. It will be appreciated that when the lag screw is threaded into position in bone fragment B, the lag screw shaft 12 will be secure within bone fragment A. For reasons which will soon be apparent, the lag screw shaft 12 is provided with a threaded axial bore 16 and a longitudinal groove or keyway 18a on its outer surface.

With continued reference to FIG. 2, it will further be observed that the angled slide member 20 comprises a first leg 22 and a second leg 24 (both of substantially cylindrical cross section in the form shown) disposed at an angle relative to each other. The particular orientation of legs 22 and 24 will naturally vary depending upon the particular fracture configuration to be treated but will typically be an angle in the range of 90°–150°. The first leg 22 of the angled slide member has an axial bore 26 through its length which is adapted at one end (the end opposite the vertex of slide member 20) to receive the lag screw shaft 12. Leg 22 may thus be inserted into the femur proximally of the subtrochanteric fracture for engagement with the lag screw shaft 12 as shown in FIG. 1. To ensure proper alignment of the lag screw shaft 12 and bore 26, the bore includes an inwardly projecting key 18b for cooperation with the previously mentioned keyway 18a on the outer surface of lag screw shaft 12. The opposite end of bore 26 is adapted to receive a compression screw 60. Preferably, bore 26 also includes an intermediate portion 28 of reduced diameter which forms a shoulder 30 within the bore which serves as a stop for the head of compression screw 60. The shaft of compression screw 60 is adapted to pass through the reduced diameter portion 28 for engagement with the threaded axial bore 16 in the lag screw shaft 12. It will therefore be appreciated that by threading the compression screw 60 into the threaded axial bore 16, the lag screw 10 and the first leg 22 of the angled slide member may be drawn tightly together to apply a compressive force between the bone fragments A and B (i.e., across the intertrochanteric fracture surface).

To prevent any shifting of the lag screw shaft 12 within leg 22 of the angled slide member once compression screw 60 has been threaded in place, and more particularly, to prevent lateral displacement of the intertrochanteric fracture fragments A and B on the subtrochanteric fragment C with weight bearing, locking means such as a locking screw 62 is inserted rearward of screw 60 in bore 26. As shown in FIG. 1, the bore 26 is adapted to threadably receive locking screw 62 rearward of compression screw 60 so that the locking screw 62 may be threaded into firm abutment against the head of the screw 60. Of course, any of a variety of locking elements (such as a keyed metal disk which is rotated into a locked position within bore 26) could be used in place of locking means for the described purpose.

To complete the fixation of the fractured bone shown in FIG. 1, the barrelled side plate 40 and the second leg 24 of the angled slide member are coupled in a manner now to be described. In accordance with the preferred form of the invention shown, barrelled side plate 40 is a retaining member of substantially cylindrical configuration which is adapted to be attached to bone fragment C by means of fixation screws 64. Fixation screws 64 thread into bone segment C through holes such as 50 in projecting flanges 48 on the body of the barrelled side plate 40.

Similarly to the first leg 22 of the angled slide member, the barrelled side plate 40 includes an axial bore 42 through its length. The bore 42 is adapted at one of its ends (the upper end as shown in the drawing) to slidably (or, more specifically, telescopically) receive the second leg 24 of the angled slide member. Bore 42 is further adapted at its opposite end to receive an additional compression screw 66. Appropriate alignment between the second leg 24 of the angled slide member and the barrelled side plate 40 is ensured by a key 32b which projects into bore 42 for cooperation with a longitudinal groove or keyway 32a on the outer surface of the second leg 24. In practice, the key 32b and keyway 32a may be arranged with different rotational alignments to permit the application of varying degrees of torsion to longitudinally adjacent bone fragments such as fragments A and B.

Preferably, as was the case with bore 26, the bore 42 in barrelled side plate 40 includes an intermediate portion 44 of reduced diameter that forms a shoulder 46 within the bore which acts as a stop for the head of compression screw 66 as is shown in FIG. 1. The shaft of compression screw 66 is adapted to pass through the reduced diameter portion 44 for engagement with a threaded axial bore 34 in the second leg 24 of the angled slide member (see FIG. 1). Thus it will be apparent that by threading the compression screw 66 into the threaded axial bore 34, the second leg 24 of the angled slide member and the barrelled side plate 40 will be drawn tightly together. This action, of course, serves to apply a compressive force between the bone segments A and C (i.e., across the subtrochanteric fracture site). It should be noted that in the case of compression screw 66, it is preferable not to provide a locking screw or the like as was done in connection with compression screw 60. This permits rearward movement of the compression screw 66 within bore 42 so that additional dynamic compressive loading may occur at the subtrochanteric fracture site with weight bearing, thereby further enhancing the healing process.

From the preceding discussion it will be appreciated that by virtue of the invention, rigid fixation of the multiply fractured femur in FIG. 1 is achieved in conformity with the basic considerations set forth at the outset hereof. More specifically, the cooperable assembly of the slide member 20 and the side plate 40 provide the desired compressive force at the subtrochanteric fracture site while shear, rotational and angular stresses at the fracture site are substantially eliminated as a result of the general geometry of the axial compression device. A similar effect is achieved at the intertrochanteric fracture site by the cooperative relationship of the lag screw 10 and the slide member 20.

While a preferred form of the invention has been shown and described, it will be appreciated by those skilled in the art that numerous modifications may be made according to the principles of the invention, the scope of which is defined in the appended claims. For example, it may be desirable in various situations to use components of different configurations from those shown (i.e., components of non-cylindrical cross section). In addition, it may be beneficial in some situations to provide additional fixation means whereby the slide member may be attached directly to one of the fractured bone fragments. It may further be desirable for certain applications to include a ratcheting mechanism for the slide member and compression slide to prevent disengagement thereof.

I claim as my invention:

1. An axial compression device for the fixation of a fractured bone having a first bone fragment, a second bone fragment disposed transverse to the first bone fragment and a third bone fragment disposed longitudinally of the first bone fragment, comprising:
    (a) first means constructed to be secured to said second bone fragment,
    (b) second means, including a slide member cooperable with said first means, configured to receive a compression means for compressing said first and second bone fragments, and
    (c) a retaining member constructed to be secured to said third bone fragment and having an axial engagement means extending threralong which is configured at one end to slidably engage a leg of said slide member and at an opposite end to receive another compression means for compressing said first and said third bone fragments longitudinally.

2. An axial compression device as recited in claim 1, wherein said first means comprises a lag screw having a shaft with a threaded axial bore therein and wherein said slide member is an angled member including a first leg and a second leg, the first leg having an axial bore extending therethrough which is configured at one of its ends to receive the shaft of said lag screw and at its opposite end to receive a compression screw threadably engageable with the threaded axial bore in the shaft of said lag screw.

3. An axial compression device as recited in claim 2, wherein the second leg of said angled slide member has a threaded axial bore therein and wherein said engagement means comprises an axial bore which extends through said retaining member and which is configured at one of its ends to slidably receive the second leg of said angled slide member and at its opposite end to receive an additional compression screw threadably engageable with the threaded axial bore in the second leg of said angled slide member.

4. An axial compression device as recited in claim 3, wherein the axial bore extending through said retaining member has an intermediate portion of reduced diameter which forms a shoulder within that bore and wherein said additional compression screw has a shaft portion constructed to pass through said intermediate portion of reduced diameter for engagement with the threaded axial bore in the second leg of said angled slide member and a head portion constructed to abut the shoulder formed by said intermediate portion of reduced diameter.

5. An axial compression device as recited in claim 4, wherein the axial bore extending through the first leg of said angled slide member has another intermediate portion of reduced diameter which forms a shoulder within that bore and wherein the first mentioned compression screw has a shaft portion constructed to pass through said another intermediate portion of reduced diameter for engagement with the threaded axial bore in the shaft of said lag screw and a head portion constructedto abut the shoulder formed by that intermediate portion of reduced diameter.

6. An axial compression device as recited in claim 5, wherein the axial bore extending through the first leg of said angled slide member is further configured at its said opposite end to receive locking means for preventing shifting of the first mentioned compression screw.

7. An axial compression device as recited in claim 6, wherein said locking means comprises an additional screw to threadably engageable with the axial bore extending through the first leg of said angled slide member rearwardly of the first mentioned compression screw.

8. An axial compression device as recited in claim 3, wherein the axial bore extending through the first leg of said angled slide member and the shaft of said lag screw are provided with cooperable key and keyway means for aligning the same, wherein the axial bore extending through said retaining member and the second leg of said angled slide member are provided with additonal cooperable key and keyway means for aligning the same, and wherein said retaining member has means defining holes therein for receiving fixation screws for attachment to said third bone fragment.

9. An axial compression device for the fixation of a fractured bone having a first bone fragment and a second bone fragment disposed longitudinally of the first bone fragment, comprising:
    (a) shaft means constructed to be secured within said first bone fragment,
    (b) an angled slide member having a first leg for connection to said shaft means and a second leg, and
    (c) a retaining member constructed to be secured to said second bone fragment and having axial engagement means extending therealong which is configured at one end to slidably engage said second leg of said slide member and at an opposite end to receive a compression means for compressing said first and second bone fragments longitudinally.

10. An axial compression device as recited in claim 9, wherein said shaft means comprises a lag screw having a shaft with a threaded axial bore therein and wherein the first leg of said angled slide member has an axial bore extending therethrough which is configured at one of its ends to receive the shaft of said lag screw and at its opposite end to receive a compression screw threadably engageable with the threaded axial bore in the shaft of said lag screw.

11. An axial compression device as recited in claim 10, wherein the second leg of said angled slide member has a threaded axial bore therein and wherein said engagement means comprises an axial bore which extends through said retaining member and which is adpated at one of its ends to receive the second leg of said angled slide member and at its opposite end to received an additional compression screw threadably engageable with the threaded axial bore in the second leg of said angled slide member.

12. An axial compression device as recited in claim 11, wherein the axial bore extending through said retaining member has an intermediate portion of reduced diameter which forms a shoulder within that bore and wherein said additional compression screw has a shaft portion constructed to pass through said intermediate portion of reduced diameter for engagement with the threaded axial bore in the second leg of said angled slide member and a head portion constructed to abut the shoulder formed by said intermediate portion of reduced diameter.

13. An axial compression device as recited in claim 12, wherein the axial bore extending through the first leg of said angled slide member has another intermediate portion of reduced diameter which forms a shoulder within that bore and wherein the first mentioned compression screw has a shaft portion constructed to pass through said another intermediate portion of reduced diameter for engagement with the threaded axial bore in the shaft of said lag screw and a head portion constructed to abut the shoulder formed by that intermediate portion of reduced diameter.

14. An axial compression device as recited in claim 13, wherein the axial bore extending through the first leg of said angled slide member is further configured at its said opposite end to receive locking means for preventing shifting of the first mentioned compression screw.

15. An axial compression device as recited in claim 14, wherein said locking means comprises an additional screw threadably engageable with the axial bore extending through the first leg of said angled slide member rearwardly of the first mentioned compression screw.

16. An axial compression device as recited in claim 11, wherein the bore extending through the first leg of said angled slide member and the shaft of said lag screw are provided with cooperable key and keyway means for aligning the same, wherein the bore extending through said retaining member and the second leg of said angled slide member are provided with additional cooperable key and keyway means for aligning the same, and wherein said retaining member includes means defining holes therein for receiving fixation screws for attachment to said second bone fragment.

17. For use in an axial compression device for the fixation of a fractured bone having a first bone fragment and a second bone fragment, an assembly comprising:
 (a) an angled slide member having a first leg for connection to said first bone fragment and a second leg, and
 (b) a retaining member constructed to be secured to said second bone fragment and having an axial engagement means extending therealong which is configured at one end to slidably engage said second leg of said angled slide member and at an opposite end to receive a compression means for compressing said first and second bone fragments longitudinally.

18. The assembly as recited in claim 17, wherein the second leg of said angled slide member has a threaded axial bore therein and wherein said engagement means comprises an axial bore which extends through said retaining member and which is configured at one of its ends to slidably receive the second leg of said angled slide member and at its opposite end to receive a compression screw threadably engageable with the threaded axial bore in the second leg of said angled slide member.

19. An axial compression device as recited in claim 18, wherein the axial bore extending through said retaining member has an intermediate portion of reduced diameter which forma s shoulder within that bore and wherein said compression screw has a shaft portion constructed to pass through said intermediate portion of reduced diameter for engagement with the threaded axial bore in the second leg of said angled slide member and a head portion constructed to abut the shoulder formed by said intermediate portion of reduced diameter.

20. An axial compression device as recited in claim 18, wherein the bore extending through said retaining member and the second leg of said angled slide member are provided with cooperable key and keyway means for aligning the same and wherein said retaining member includes means defining holes therein for receiving fixation screws for attachment to said second bone fragment.

* * * * *